United States Patent
Spinello

(10) Patent No.: US 6,629,958 B1
(45) Date of Patent: Oct. 7, 2003

(54) LEAK SEALING NEEDLE

(76) Inventor: Ronald P. Spinello, 4169 Sycamore La., Red Lion, PA (US) 17356

( * ) Notice: Subject to any disclaimer, the term of this patent is extended or adjusted under 35 U.S.C. 154(b) by 46 days.

(21) Appl. No.: 09/589,317

(22) Filed: Jun. 7, 2000

(51) Int. Cl.⁷ .......................................... A61M 29/00
(52) U.S. Cl. ..................... 604/192; 604/198; 433/215
(58) Field of Search ............................. 604/93.01, 158, 604/161–165, 164.01, 164.06, 164.12, 171, 172, 187, 264, 265, 272, 239, 192, 198; 606/92, 93; 433/215; 428/373; 524/731; 424/422

(56) References Cited

U.S. PATENT DOCUMENTS

| | | | | |
|---|---|---|---|---|
| 881,469 A | * | 3/1908 | Hale ........................ 604/239 |
| 2,888,924 A | | 6/1959 | Dunmire .................. 604/199 |
| 3,134,380 A | | 5/1964 | Armao |
| 3,354,881 A | | 11/1967 | Bloch ........................ 604/198 |
| 3,585,984 A | | 6/1971 | Buchanan ................. 600/577 |
| 3,734,080 A | * | 5/1973 | Petterson et al. ........... 600/577 |
| 3,882,863 A | * | 5/1975 | Sarnoff et al. .............. 604/136 |
| 3,920,001 A | * | 11/1975 | Edwards ................... 600/577 |
| 4,154,229 A | | 5/1979 | Nugent |
| 4,411,655 A | * | 10/1983 | Schreck .................... 604/165 |
| 4,416,290 A | | 11/1983 | Lutkowski |
| 4,416,663 A | | 11/1983 | Hall |
| 4,463,127 A | * | 7/1984 | Alberts et al. .............. 524/731 |
| 4,725,267 A | * | 2/1988 | Vaillancourt ............... 604/192 |
| 4,795,432 A | * | 1/1989 | Karczmer .................. 604/198 |
| 4,804,371 A | * | 2/1989 | Vaillancourt ............... 604/198 |
| 4,828,547 A | * | 5/1989 | Sahi et al. .................. 604/164 |
| 4,850,996 A | | 7/1989 | Cree ........................ 604/198 |
| 4,887,998 A | * | 12/1989 | Martin et al. .............. 604/198 |
| 4,915,697 A | | 4/1990 | DuPont .................... 604/192 |
| 4,935,012 A | * | 6/1990 | Magre et al. .............. 604/192 |
| 4,943,282 A | | 7/1990 | Page et al. |
| 5,015,240 A | | 5/1991 | Soproni et al. ............ 604/192 |
| 5,070,885 A | | 12/1991 | Bonaldo |
| 5,122,123 A | * | 6/1992 | Vaillancourt ............... 604/192 |
| 5,141,748 A | * | 8/1992 | Rizzo ........................ 424/422 |
| 5,185,006 A | * | 2/1993 | Williamitis et al. ......... 604/265 |
| 5,193,552 A | | 3/1993 | Columbus et al. |
| 5,222,505 A | | 6/1993 | Burns |
| 5,242,418 A | * | 9/1993 | Weinstein .................. 604/192 |
| 5,356,387 A | * | 10/1994 | Sirbola ...................... 604/198 |
| 5,423,758 A | | 6/1995 | Shaw ........................ 604/195 |
| 5,501,666 A | | 3/1996 | Spielberg |
| 5,518,004 A | | 5/1996 | Schraga |
| 5,527,297 A | | 6/1996 | Paul |
| 5,549,568 A | * | 8/1996 | Shields ...................... 604/192 |
| 5,569,189 A | | 10/1996 | Parsons |
| 5,569,190 A | | 10/1996 | D'Antonio |
| 5,569,286 A | | 10/1996 | Peckham et al. |
| 5,573,513 A | | 11/1996 | Wozencroft |
| 5,601,536 A | * | 2/1997 | Crawford et al. ........... 604/198 |
| 5,658,256 A | * | 8/1997 | Shields ...................... 604/192 |
| 5,687,740 A | | 11/1997 | Sheridan |
| 5,695,474 A | | 12/1997 | Daugherty |
| 5,730,723 A | | 3/1998 | Castellano et al. |
| 5,746,714 A | | 5/1998 | Salo et al. |
| 5,755,696 A | | 5/1998 | Caizza ...................... 604/164 |
| 5,769,826 A | | 6/1998 | Johnson et al. |
| 5,776,107 A | | 7/1998 | Cherif-Cheikh |
| 5,782,802 A | | 7/1998 | Landau |
| 5,792,122 A | | 8/1998 | Brimhall et al. |

(List continued on next page.)

Primary Examiner—Thomas Denion
Assistant Examiner—Thai-Ba Trieu
(74) Attorney, Agent, or Firm—Galgano & Burke

(57) ABSTRACT

A hypodermic needle structure for making shallow injections of local anesthetic into human tissue under relatively high pressure in which an elastomeric sheath on the needle shank bears against the punctured tissue immediately surrounding the needle shank to form a pressure seal against leakage of the anesthetic liquid and of the puncture hole to facilitate the maintenance of relatively high liquid pressures at the lumen of the needle while the liquid works its way through connected tissue to the targeted nerve site.

11 Claims, 3 Drawing Sheets

U.S. PATENT DOCUMENTS

| | | |
|---|---|---|
| 5,800,395 A | 9/1998 | Botich et al. |
| 5,810,775 A | 9/1998 | Shaw |
| 5,817,058 A | 10/1998 | Shaw .......................... 604/198 |
| 5,885,255 A * | 3/1999 | Jaeger, Jr. et al. .......... 604/192 |
| 5,911,703 A | 6/1999 | Slate et al. |
| 5,919,159 A | 7/1999 | Lilley et al. |
| 5,938,637 A | 8/1999 | Austin et al. |
| 5,947,836 A | 9/1999 | Murphy et al. ............. 473/300 |
| 5,957,886 A | 9/1999 | Weston |
| 6,004,286 A | 12/1999 | Bellhouse et al. |
| 6,010,487 A | 1/2000 | DeMichele et al. |
| 6,013,050 A | 1/2000 | Bellhouse et al. |
| 6,024,710 A | 2/2000 | Miller ........................ 604/195 |

* cited by examiner

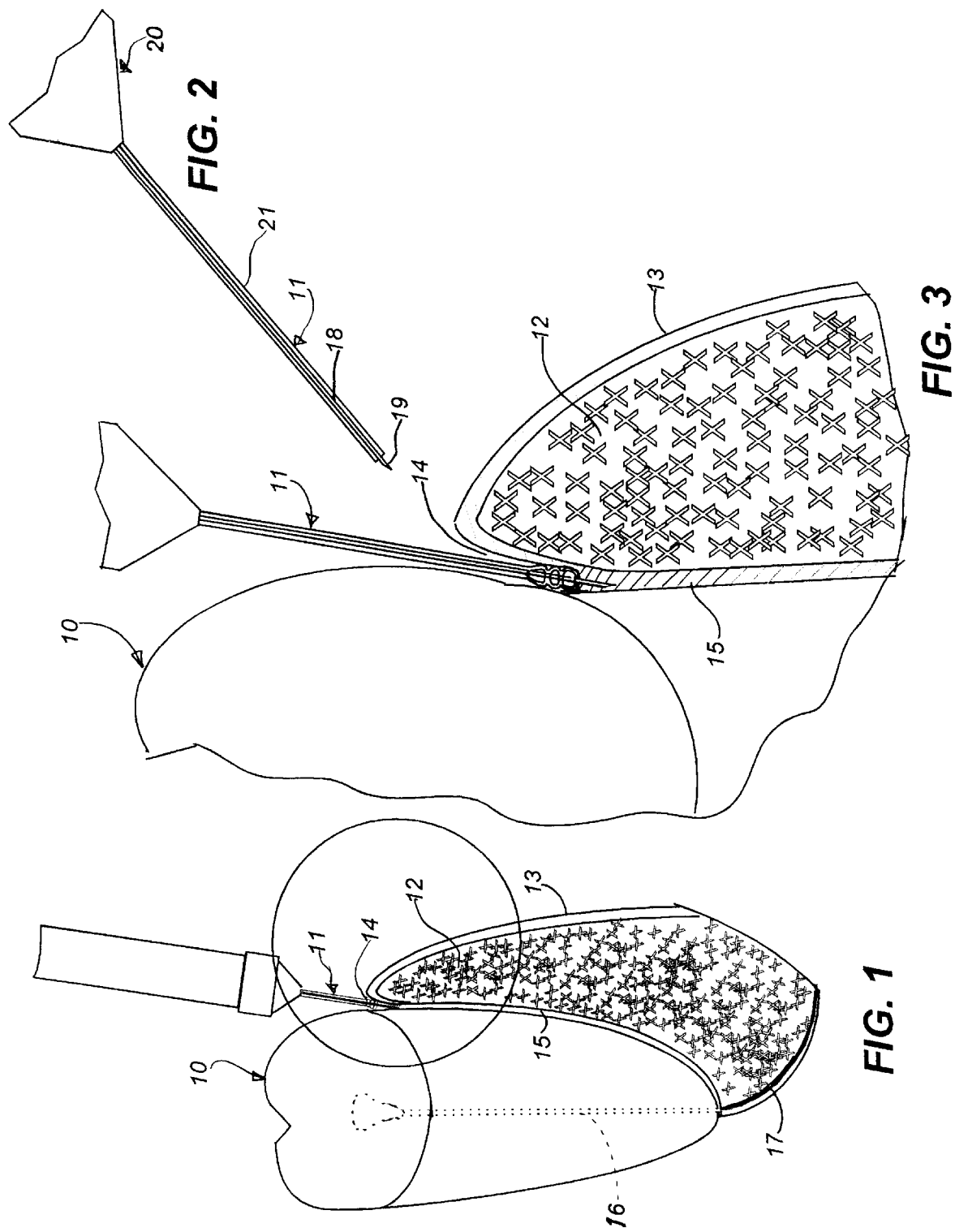

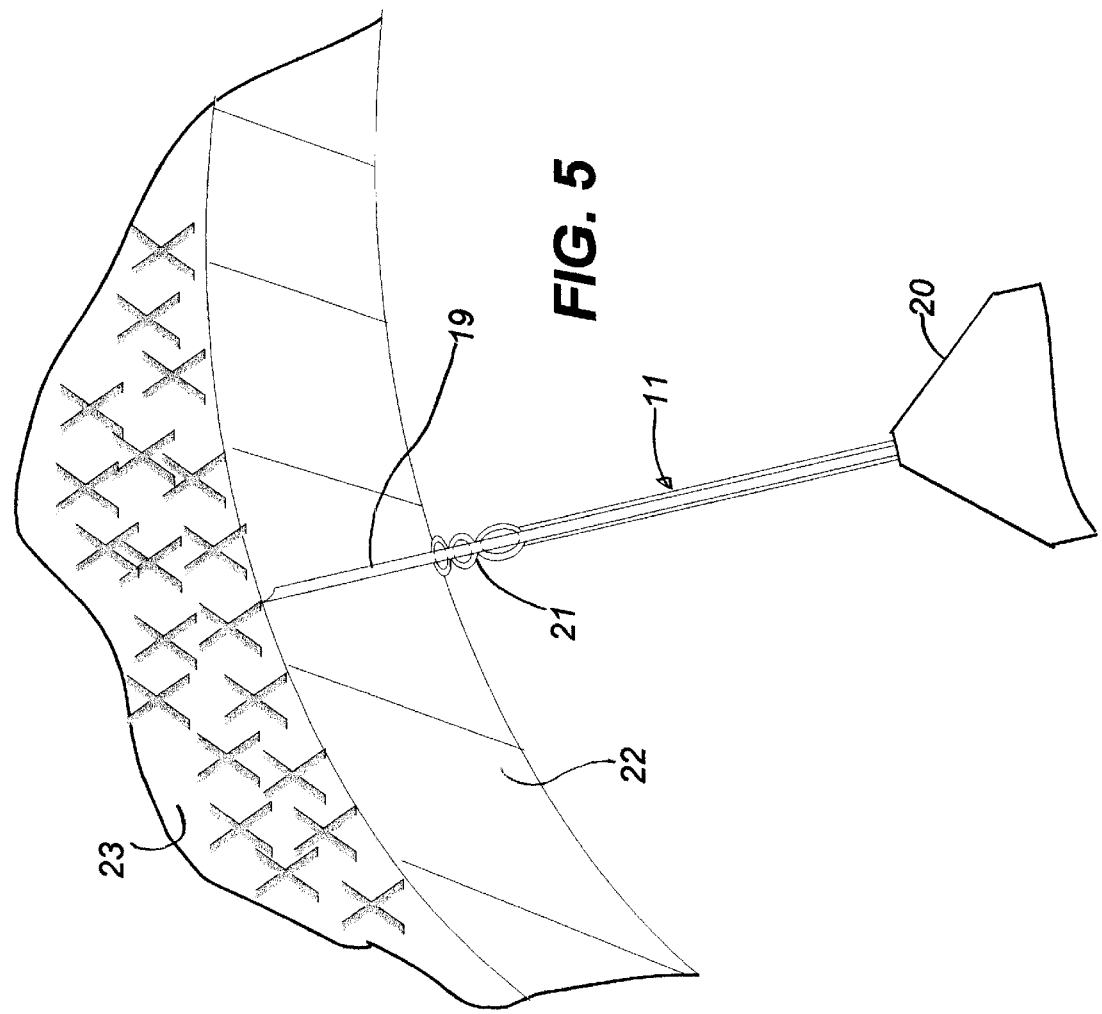
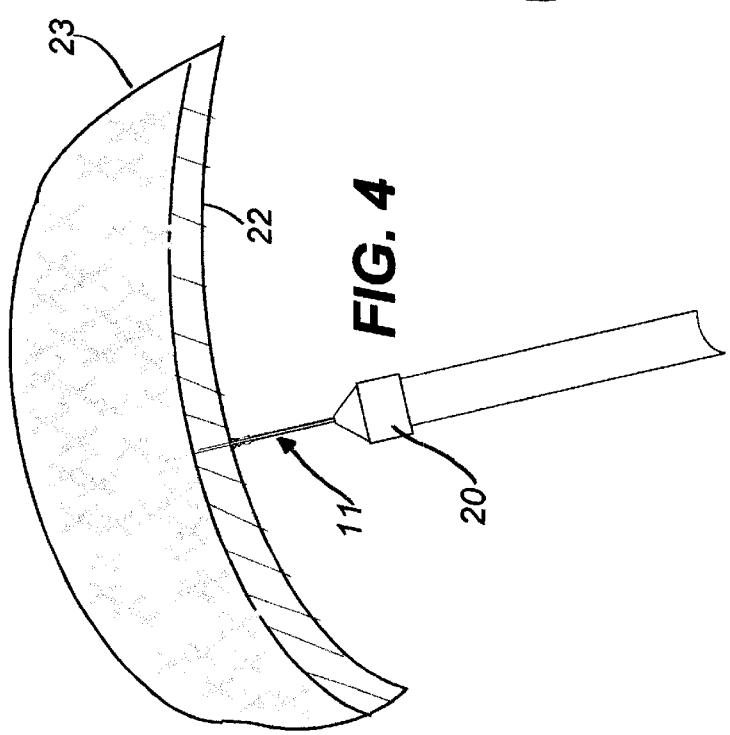

LEAK SEALING NEEDLE

FIELD OF THE INVENTION

The invention is a hypodermic needle assembly for the injection of local anesthetic, or other therapeutic fluid, into the tissue under pressure, particularly where the needle penetration is shallow.

BACKGROUND OF THE INVENTION

At least three known shallow injections of local anesthetic used in dentistry are wonderfully effective when they work but can be difficult for the doctor to perform and uncertain in their results. They are known as 1) the periodontic ligament (PDL) injection where the gingival tissue meets each tooth across the thin band of ligament which ties all teeth to the bone; 2) the intrapulpal injection through an opening in the tooth enamel into the pulp chamber of the tooth hoping, of course, to find the root canal; and 3) the palatal or anterior middle superior alveolar (AMSA) injection in the shallow tissue of the roof of the mouth, believed to have been first discovered by the applicant, and dedicated to the public domain in 1996.

The earlier discovery by the applicant of apparatus and method by means of which many injections of local anesthetic can be performed substantially free of pain is disclosed in U.S. Pat. Nos. 4,747,824 and 5,180,371 and, using a different approach, in pending U.S. applications Ser. Nos. 09/122,915 and 09/394,958. These inventions all utilize precisely controlled flow rates for local anesthetic into the tissues over a wide range of pressures demanded by the equally wide range of tissue densities and distances which must be overcome in the body between the point of discharge of the anesthetic at the lumen of the implanted needle and the targeted nerves to be disabled to effect local numbing. Not infrequently, however, in shallow injections, the time for numbing to occur is prolonged or worse, never occurs, even though modern technology has made the procedure more bearable for the patient.

SUMMARY OF THE INVENTION

The present invention has for its purpose to improve measurably the success rate of local anesthetic injections, particularly when the hypodermic needle is implanted in shallow sites. In accordance with the invention, the shank of the needle is enveloped and enlarged by a sheath or lamination of elastomeric material with the interface between the sheath and the needle shank being such that at least the forward portion of the sheath can be slid backward when pressed from the forward end. The sliding motion is countered further back along the shank. Thus the sharp needle can cut its way into the tissue while the tissue surrounding the puncture hole engages the sheath to cause compression against the inherent elasticity. The sheath then forms a pressure seal around the needle shank where it enters the tissue.

When an injection is shallow, there is created a likely shunt path for leakage flow of anesthetic liquid under pressure out of the hole made by the needle. This leakage path is particularly vulnerable as the pressure on the anesthetic liquid is raised in an attempt to drive it through the interior tissues to the targeted nerve site. This leakage path is, however, sealed by the elastomeric sheath so that the pressure of local anesthetic is maintained over a wide range of injection pressures, while the injection apparatus continues to furnish its predetermined, controlled flow rate.

THE PRIOR ART

Elastomeric sleeves have been used for years, in a different way for a different purpose, in the practice of phlebotomy in which veins are tapped for obtaining blood samples. See U.S. Pat. Nos. 3,585,984 and 6,024,710 inter alia. A hollow needle is inserted in a vein so that blood flows naturally out of the back end to be collected in a specimen vial. The vial was evacuated and covered by a sealing membrane to boost the natural flow and to reduce the oxygen to which the sample is exposed. An elastomeric sleeve was added to the back end of the needle to act as a simple valve covering the discharge to keep blood from dripping out when no specimen vial is in place. The sleeve valve opens when pushed back by the puncturable sealing membrane covering the vial.

As such, the prior art is structurally and functionally different from the present invention in which the elastomeric sleeve is a pressure seal fitted on the front shank of a high pressure injection needle itself and which blocks the leakage flow path of local anesthetic discharged from the needle and flowing backward along the shank of the needle in the hole made in the tissue by the needle. The critical pressure seal is effected on the surface of the very tissue penetrated by the needle.

BRIEF DESCRIPTION OF THE DRAWINGS

FIG. 1 is a side view of a bicuspid tooth in the lower jaw and, in cross-section part of the jaw bone, the gingival tissue covering the bone and the periodontal ligament by means of which the tooth is anchored in the bone. Also shown in side view is the front portion of a hypodermic needle assembly in which the tip of the needle is inserted into the periodontal ligament at the base of the gingival trough.

FIG. 2 is a side view in enlarged scale of the front end of a hypodermic needle assembly of FIG. 1 showing the needle sheath of elastomeric material in cross-section and terminated a short distance from the sharpened point.

FIG. 3 is an enlarged view of a portion of FIG. 1 showing the hypodermic needle tip penetrating the gingival trough and the periodontal ligament for a sufficient distance to cause axial compression of the elastomeric sheath.

FIG. 4 is a view in cross-section of a fragment of the roof of the mouth and showing a sheathed or laminated hypodermic needle penetrating the mucous membrane tissue to the bone and with the sheath under compression at the surface of the mucous membrane tissue.

FIG. 5 is an enlarged view of a portion of FIG. 4 showing, in particular, the compression action of the elastomeric sheath.

BRIEF DESCRIPTION OF THE PREFERRED EMBODIMENTS

Figure 7:
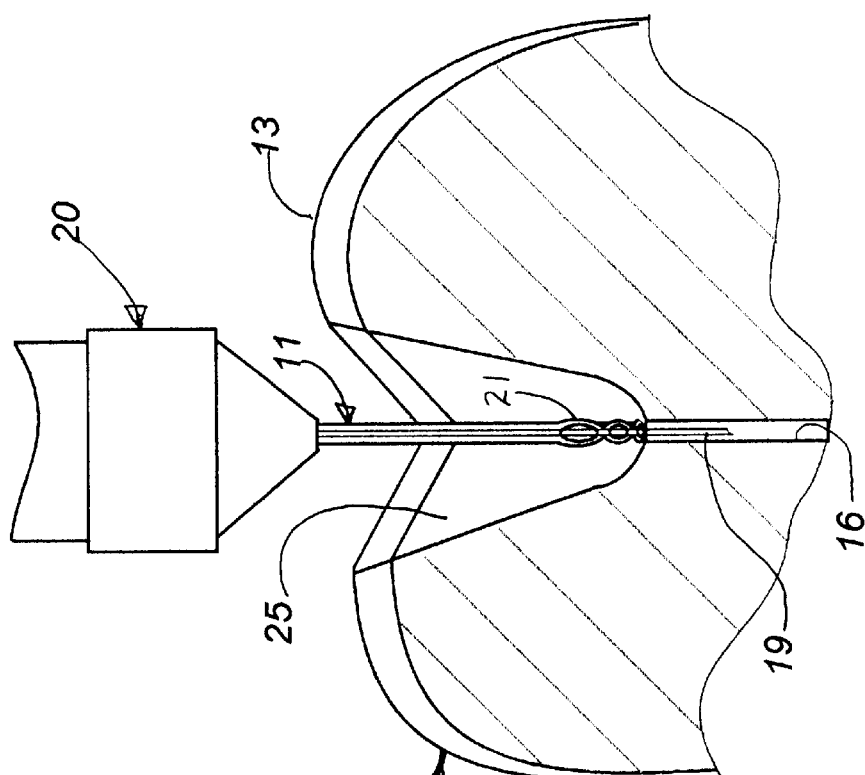
FIG. 7 is an enlarged view of a portion of FIG. 6 showing the action of the elastomeric sheath when the needle tip enters the root canal.

Referring to FIGS. 1–3, there is shown a bicuspid tooth 10 in the process of receiving a periodontal ligament (PDL) injection of local anesthetic from a hypodermic needle assembly 11 described more fully below. Only the front end of the hypodermic syringe assembly is shown, it being understood that the entire syringe can take the form of a conventional thumb- or hand-actuated piston syringe or a modern pencil-like unit using a remote pump of the type shown in the applicant's patents and applications cited above.

The tooth 10 is seated in jaw bone 12, the outer portion of which is covered by a layer of gingival tissue 13, which also defines a gingival trough 14 closely adjacent the wall of the tooth. The tooth 10, like all others, is held in its bone socket by a thin sheet of periodontal ligament 15. Deep in the tooth is a root canal 16, housing the tooth's nerve system 17 which exits the tooth at the base of the root to enter the jaw bone on its way to the brain.

One very effective but historically difficult medical procedure for anesthetizing a single tooth is to subject this nerve system to local anesthetic liquid where it emerges from the base of the root canal. This can be done by means of the periodontal ligament (PDL) injection in which the tip of the hypodermic needle is implanted in the ligament 15 where it meets the gingival trough 14, as shown in FIGS. 1 and 3. Very high pressure on the liquid anesthetic, for example up to 28 pounds of force on the piston of a conventional vial of anesthetic, is required to move the anesthetic down the ligament space and through the socket bone to find paths to the nerve system 17 far below. It is this characteristic that makes the injection difficult to perform safely manually.

The applicant's patents and patent applications cited above provide the means to furnish controlled flow rates for the anesthetic over wide pressure ranges that make the periodontal ligament (PDL) a viable, safe medical tool in dentistry. But the fact remains that up to 15% to 20% of the new procedures fail at least to some extent to achieve profound anesthesia of the tooth. The present invention identifies the failure problem as one of controlling and maintaining liquid pressure of the anesthetic within the tissue. Leakage of the pressurized liquid from the discharge lumen of the needle back along the implanted shank of the needle and out of the hole made by the needle entering the tissue can drop the pressure below that needed to drive the liquid to the targeted nerve site.

The invention for preventing such leakage is shown in FIG. 2 as a needle assembly 11 including a conventional hollow needle 18 with a beveled tip 19 and secured at its inner end in a handle 20. Local anesthetic is delivered to the needle either in a cylinder and piston configuration in the barrel of the handle (not shown) or by means of a remote pumping system as disclosed in the applicant's cited patents and applications. Surrounding the needle 18 is an elastomeric sheath 21 which terminates at a point close to the tip 19. The short portion 19 of the needle projection from the sheath 21, on the order of 1 to 3 mm, is selected to render the tip just visible to the dentist to facilitate accurate implantation of the needle in the body but inconspicuous to the patient for psychological purposes.

The elastomeric sheath 21 is slidable on the shank of the needle and its spacing from the needle tip is also selected with care to insure that it is less than the minimum depth contemplated for the implantation of the needle before the flow of local anesthetic is begun. Referring to FIG. 3, the needle assembly is shown implanted shallowly in the periodontic ligament 15 at the base of the gingival trough 14. The front end of the sheath 21 has been pushed back by and bears resiliently against the tissue immediately surrounding the shaft of the needle. This structure forms the pressure seal against the escape by leakage of the liquid from the discharge lumen at the tip of the needle backward along the shank of the needle to escape into the mouth (unpleasant at best) and thus maintains the internal pressure necessary to cause the anesthetic to work its way down a highly resistant path to the buried nerves coming out of the root of the tooth.

Another shallow injection using the same hypodermic needle construction (identified by the same reference numbers above) is shown in FIGS. 4 and 5 which show in cross section a fragment of the roof of the mouth in which a thin layer of mucous membrane tissue 22 covers bone structure 23. This injection is known as the anterior middle superior alveolar (AMSA) injection and is carefully sited in either the left hand or right hand forward quadrant of the roof of the mouth to reach nerve bundles in the underlying bone serving all the teeth in the quadrant, and thus numbs a plurality of teeth at one shot.

The needle tip 19 is carefully implanted shallowly into the mucous membrane tissue 22 until it reaches the bone 23. The forward end of the elastomeric sleeve 21 has engaged the exposed tissue on the roof of the mouth and been compressed thereby against its own elasticity so that it exerts sealing pressure around the needle shank where it enters the tissue. Under pressures ranging from approximately 28 pounds of force (on the piston of a conventional vial of anesthetic) the liquid local anesthetic will be forced laterally through the tissue and its interface with the bone to reach the nerve site (not shown) while the compressed elastomeric sleeve 20 blocks leakage flow into the mouth through the needle puncture.

Figure 6:
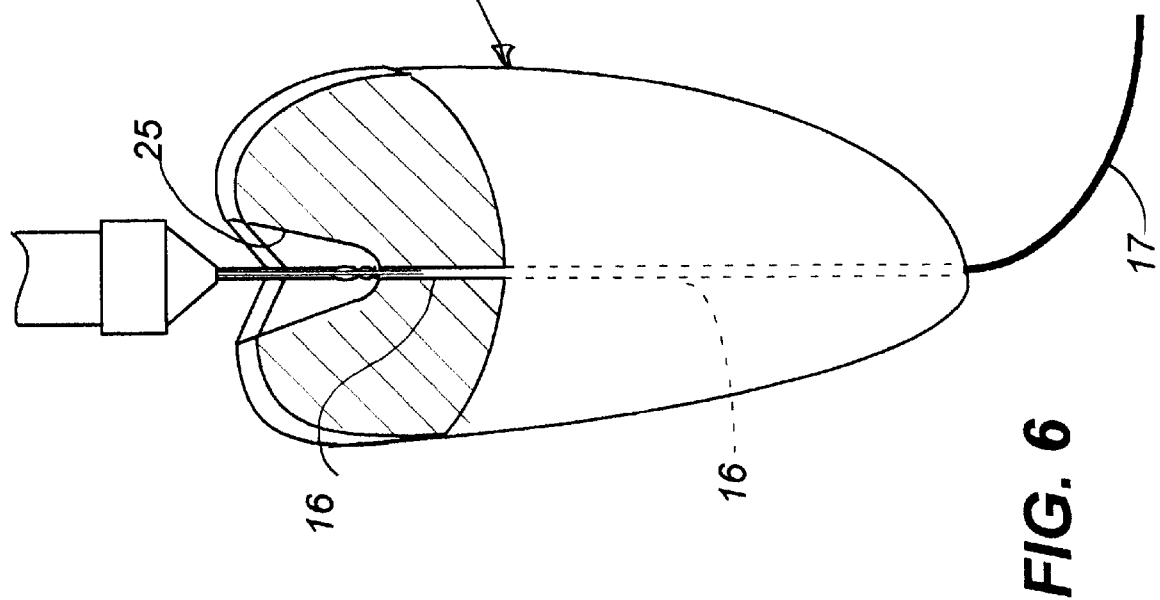
FIG. 6 is a side view of a bicuspid tooth under root canal treatment with the outer portion shown in cross-section to show a prepared opening (which was once a cavity) in the pulpal interior to expose the root canal and in which a sheathed needle has been inserted into the root canal.

Referring to FIGS. 6 and 7, the new needle structure is shown in the process of an intrapulpal injection directly into a tooth 24. The decay material in the pulp of the tooth is shown as removed (by dental drilling) to form a pulpal chamber 25 which communicates with the root canal 16. The tooth having been previously anesthetized to the extent possible by, for example, an AMSA injection. Much residual pain can nevertheless remain in an infected tooth associated with decay and inflammation deep in the root canal (which is why the canal must be opened, treated, cleaned and packed in a procedure loosely defined as root canal or endodontic treatment). Before undertaking such deep treatment, the dentist will sometimes resort to an intrapulpal injection in which local anesthetic is driven directly into the root canal via the drilled out cavity space. Leakage can occur as often as not in this particular procedure and the present invention significantly improves the rate of successful treatment.

As best seen in FIG. 7, the front portion 19 of the needle has found the root canal 16 for a short distance and the elastomeric sheath 21 has found a bearing at the upper end of the root canal to be compressed thereby. A pressure seal is therefore formed at the upper end of the root canal and even though there is substantial clearance between the outside diameter of the needle shank and the wall of the root canal (forming an obvious leakage path). The local anesthetic forced into the root canal under pressure will not back up into the mouth of the patient and thus fall below that necessary to drive it down the infected root canal.

It will be understood that the invention can be used in any injection situation in which maintaining pressure at the needle point is helpful to the procedure or in which the avoidance of distasteful local anesthetic in the mouth is advantageous.

The fabrication of a hypodermic needle assembly in accordance with the present invention can be achieved in several ways. The elastomeric compound can be applied to the needle shank by spraying on or dipping in the compound in its uncured state. In the case of dipping, the desired bare end tip, (if any such is desired) can be achieved by pressing the point of the dipped needle into an absorbent medium to the desired depth such for example as 1–3 mm. A typical compound for spraying or dipping is comprised of polydimethyl vinyl siloxane, polydimethyl hydrogen siloxane, silica and paraffin and sold by Discus Dental, Inc. of Los Angeles, Calif., for example, under its trademark HALF TIME and activated immediately before use. Also, the needle shanks can be treated beforehand with any of the coating lubricants commonly used on needles to ease the implanting and withdrawing action to act as a parting agent so that sleeve when cured will slide easily on the needle shank. The wall thickness of the sleeves can be in the range of 0.3 mm to 1.5 mm and the internal diameter of the sleeve can be approximately that of the o.d. of the needle or slightly larger.

The invention will perform its pressure sealing function even if the entire needle including the point is at the outset covered with the elastomeric sheath. In this case, the doctor will be unable to see the point of the needle until it is pressed through the end of the sheath as the injection procedure is undertaken. Also, the elastomeric cylindrical sheath can be prefabricated as a unit before assembly on the needle by simply threading it in place. It will be understood that the sliding movement on the shank of the needle by the elastomeric sheath affords tolerance for greater variation in the depth of needle implantation. If, however, the depth of penetration is known, the sliding movement on the shank becomes less important because the forward end of the sleeve can be brought to bear more precisely on the tissue surrounding the needle. Lastly, it should be noted that gentle pressure brought to bear on the external tissue into which a hypodermic needle is inserted is thought to have a neurological effect that can reduce the patient's sensitivity to the implantation of the needle itself. It is possible that the elastomeric sheath of the present invention may have or might be made to have such a beneficial effect. The invention should not, therefore, be regarding as limited except as defined in the following claims.

What is claimed is:

1. A hypodermic needle assembly for the injection of therapeutic fluid into the body under pressure, comprising:

a hollow needle having a sharpened tip end with a fluid discharge lumen to penetrate a body part, a back end through which the fluid is introduced into the needle under pressure, and an elongated shank portion between the ends, and retractable and collapsible means for sealing against leakage of the injected fluid under pressure comprising a sheath of elastomeric material enveloping at least part of the shank portion adjacent the tip end, whereby inserting the needle into the body causes the sheath to bear against the punctured tissue surrounding the needle shank to form a seal against leakage of the injected fluid under pressure.

2. A hypodermic needle according to claim 1, said sheath being slidable on the needle shank at least along its forward portion, and means for resisting sliding movement at the rearward position of the sheath, whereby the forward end of the sheath can yield resiliently rearwardly on the shank to allow both further axial penetration by the needle into the body part and to apply additional axial pressure by the resilient forward end of the sleeve for sealing against leakage of fluid backward along the shank of the inserted needle.

3. A hypodermic needle assembly as set forth in claim 2 comprising a lubricating parting agent on the shank of the needle.

4. A hypodermic needle assembly as set forth in claim 2 in which the elastomeric sheath is formed on the needle shank by applying the material in its uncured liquid form to the hollow needle, the sheath being cured on the shank.

5. A hypodermic needle assembly as set forth in claim 4, the elastomeric sheath being formed of a mixture of polydimethyl vinyl siloxane, hydrogen siloxane, silica and paraffin.

6. A hypodermic needle assembly as set forth in claim 2 in which the elastomeric sheath is formed independently of the needle and threaded on the needle in its cured state.

7. A hypodermic needle according to claim 1 in which the forward end of the sheath terminates rearward of the needle tip for rendering the tip visible to facilitate the correct site of implantation of the needle point in the body part.

8. A hypodermic needle assembly according to claim 1 wherein said sheath has a thickness of up to about 1.5 millimeters.

9. A hypodermic needle assembly according to claim 1 wherein said sheath has a thickness of about 0.3 millimeters to about 1.5 millimeters.

10. A hypodermic needle assembly for the injection of therapeutic fluid into the body under pressure, comprising:

a hollow needle having a sharpened tip end with a fluid discharge lumen to penetrate a body part, a back end through which the fluid is introduced into the needle under pressure, and an elongated shank portion between the ends, and a retractable and collapsible elastomeric sheath having a wall thickness of up to about 1.5 millimeters substantially enveloping at least part of the shank portion adjacent the tip end, whereby inserting the needle into the body causes the sheath to bear against the punctured tissue surrounding the needle shank to form a seal against leakage of the injected fluid under pressure.

11. A hypodermic needle assembly according to claim 10 wherein said sheath has a wall thickness of about 0.3 millimeters to about 1.5 millimeters.

\* \* \* \* \*